United States Patent
Reddy (10) Patent No.: US 11,116,720 B2
(45) Date of Patent: Sep. 14, 2021

(54) ICE POP MEDICAMENT DELIVERY SYSTEM AND METHOD

(71) Applicant: NANTHEALTH, INC., Culver City, CA (US)

(72) Inventor: Sandip Reddy, Los Alamitos, CA (US)

(73) Assignee: NANTHEALTH, INC., Culver City, CA (US)

( * ) Notice: Subject to any disclaimer, the term of this patent is extended or adjusted under 35 U.S.C. 154(b) by 0 days.

(21) Appl. No.: 16/554,421

(22) Filed: Aug. 28, 2019

(65) Prior Publication Data

US 2020/0069580 A1 Mar. 5, 2020

Related U.S. Application Data (60) Provisional application No. 62/724,422, filed on Aug. 29, 2018.

(51) Int. Cl.
| | |
|---|---|
| *A61K 9/00* | (2006.01) |
| *A61K 47/10* | (2017.01) |
| *A61K 47/16* | (2006.01) |
| *A61K 47/20* | (2006.01) |

(52) U.S. Cl.
CPC ............ *A61K 9/0056* (2013.01); *A61K 9/006* (2013.01); *A61K 9/0031* (2013.01); *A61K 9/0034* (2013.01); *A61K 47/10* (2013.01); *A61K 47/16* (2013.01); *A61K 47/20* (2013.01)

(58) Field of Classification Search
None
See application file for complete search history.

(56) References Cited

U.S. PATENT DOCUMENTS

| 5,431,915 A | 7/1995 | Harvey et al. |
| 2005/0276942 A1 | 12/2005 | Somani et al. |
| 2007/0036861 A1* | 2/2007 | Oury ............... A61K 9/006 424/472 |
| 2014/0166028 A1* | 6/2014 | Fuisz ............... A24F 47/002 131/328 |
| 2016/0256383 A1* | 9/2016 | Allio ................ A61K 31/4453 |
| 2017/0360767 A1* | 12/2017 | Duggins ............ A61P 25/34 |

OTHER PUBLICATIONS

3YummyTumies, "Red White and Blue Jello Shots", https://www.3yummytummies.com/red-white-and-blue-jello-shots/, accessed Sep. 14, 2020 (Year: 2018).*
("Nystatin", https://www.sigmaaldrich.com/catalog/product/sigma/n6261?lang=en&region=US#:~:text=lt%20is%20also%20soluble%20in,store%20at%20%2D20%%C2%B0C, accessed Sep. 14, 2020 (Year: 2020).*
Cagnoni et al., "Modification of the pharmacokinetics of high-dose cyclophosphamide and cisplatin by antiemetics", Bone Marrow Transplantation, (1999) 24, pp. 1-4. (Year: 1999).*
Treister, Nathaniel S et al., "Chemotherapy-Induced Oral Mucositis Treatment & Management," https://emedicine.medscape.com/article/1079570-treatment, Jun. 22, 2017, 6 pages.
Unknown, "How to Make Weed Popsicles: Ingredients, video and tutorial," http://www.originalweedrecipes.com/how-to-make-weed-popsicles/, Jan. 4, 2018, 2 pages.

* cited by examiner

*Primary Examiner* — Melissa L Fisher
(74) *Attorney, Agent, or Firm* — Stetina Brunda Garred & Brucker (57) ABSTRACT

A multi-layered pharmaceutical delivery system is contemplated in which the delivery of medicaments to patients is controlled via the sequential delivery of medicaments contained within ingestible solid pharmaceutical layers, preferably frozen in a media that liquefies following ingestion by a patient so as to release the medicament when ingested by melting. A frozen ice pop embodiment is contemplated to contain an outermost ingestible pharmaceutical layer enclosing further ingestible pharmaceutical layers sequentially enclosed within that inner pharmaceutical layer. Other embodiments are contemplated in which the layers are linearly sequenced within an external container that prevents ingestion of the subsequent layers until the prior layers have been ingested.

14 Claims, 5 Drawing Sheets

ICE POP MEDICAMENT DELIVERY SYSTEM AND METHOD

CROSS-REFERENCE TO RELATED APPLICATIONS

This application claims the benefit of priority under 35 U.S.C. § 119(e) to U.S. Provisional Patent Application Ser. No. 62/724,422 filed on Aug. 29, 2018 and entitled ICE POP MEDICAMENT DELIVERY SYSTEM AND METHOD, the disclosure of which is hereby incorporated by reference in its entirety.

STATEMENT RE: FEDERALLY SPONSORED RESEARCH/DEVELOPMENT

Not Applicable

BACKGROUND

1. Technical Field

The present disclosure relates generally to the field of pharmaceutical delivery systems. More particularly, the present disclosure relates to time release systems for transmucosal pharmaceutical delivery.

2. Related Art

Transmucosal delivery of medication is a well-established route of administration. For example, many pharmaceuticals today are formulated for sublingual delivery, where the medications diffuse into the blood through the mucous membrane beneath the tongues. Likewise, many other forms of transmucosal delivery are routine, such as other oral forms like buccal (held in the cheek) or sublabial (held between the lips and the gums), urogenital administration such as via a pessary (a vaginal suppository), or rectal administration such as vie a suppository.

Most sublingual drugs today are configured to be administered as an aerosolized liquid suspension delivered via a spray, or as a dissolvable solid pill or strip that releases medication when dissolved via contact with the patient's saliva. However, these drugs may suffer from substantial deficiencies in their ability to regulate delivery of multiple components in a time release fashion, as retaining a slowly-dissolving unconformable pill or strip under the tongue for an extended period of time may present difficulties for many patients, especially children. Aerosol sprays, by their very nature, cannot be administered in a time delayed or extended fashion, except by a repeated spraying of a sequence of aerosol sprays which may comprise the same or different medicaments.

Likewise, formulation of time-release sequences of drugs for sublingual delivery may be difficult even when solid forms are used, especially given that dissolution via exposure to saliva may be especially unpredictable. Further, many illnesses may substantially affect a patient's saliva production, further contributing unpredictability for any time-release formulation of a sublingual pharmaceutical.

Furthermore, conventional methods of sublingual delivery in may be substantially more complicated when a patient suffers from certain oral conditions, especially conditions resulting in substantial oral sensitivity such as oral mucositis, which is in many cases the most common complication of many cancer therapies like chemotherapy or radiation therapy.

Therefore, novel systems for transmucosal pharmaceutical delivery are desirable.

BRIEF SUMMARY

To solve these and other problems, a pharmaceutical delivery system is contemplated, the pharmaceutical delivery system comprising at least two ingestible pharmaceutical layers, wherein each ingestible pharmaceutical layer comprises a media containing at least one layer-specific pharmaceutical agent, and wherein each ingestible pharmaceutical layer is characterized by one or more layer-specific delivery parameters associated with the layer-specific pharmaceutical agent contained within the media of that layer.

The media of at least one of the layers may comprise a number of compositions, including but not limited to ice, a frozen colloidal suspension, a frozen crystalloid solution, acetonitrile, dimethyl sulfoxide, ethanol, glycerine, or a lipid.

The layer-specific delivery parameters associated with the layer-specific pharmaceutical agent of at least one layer may be, for example, availability for transmucosal delivery into the bloodstream. Such transmucosal delivery may comprise, for example but without limitation, sublingual delivery, buccal delivery, rectal delivery, or urogenital delivery.

The configuration of the pharmaceutical delivery system maybe such that no portion of a first ingestible pharmaceutical layer is available for delivery to the patient until at least a portion of a second ingestible pharmaceutical layer has been delivered to the patient. The first pharmaceutical layer may be enclosed within the second pharmaceutical layer. The second pharmaceutical layer may surround the entire periphery of the first pharmaceutical layer. The first and second ingestible pharmaceutical layers may be arranged in sequence, possibly a therapeutically relevant sequence.

The first ingestible pharmaceutical layer and least a portion of the second ingestible pharmaceutical layer may be enclosed within an external container, and may be configured to traverse through the external container. The traversal may be via a pusher element. The traversal may be via a straw element.

At least one of the ingestible pharmaceutical layers may be solid, and may be configured to transition from a solid to a non-solid following ingestion. Such transition may comprise melting from a solid phase to a liquid phase. Such transition may comprise sublimation from a solid phase to a gas phase. Such transition may comprise dissolution from a solid into a surrounding or external fluid. Such transition may also comprise transition from a semi-solid to a fluid following ingestion.

Alternative embodiments of an ingestible delivery system for delivering pharmaceutically active agents to a patient are also contemplated, such as a system comprising a first solid media containing a first active agent, the first solid media being transitionable from a solid to a non-solid at a temperature lower than the internal body temperature of the patient such that following ingestion and subsequent transition of at least a portion of the first solid media to a first non-solid media, at least a portion of the first active agent is made available for transmucosal delivery into the bloodstream, and a second solid media containing a second active agent, the second solid media being transitionable from a solid to a non-solid at a temperature lower than the internal body temperature of the patient such that following ingestion and subsequent transition of at least a portion of the second solid media to a second non-solid media, at least a portion of the second active agent is made available for transmucosal delivery into the bloodstream, wherein the second solid media at least partially encloses the first solid media such that following ingestion of the delivery system, no portion of the first active agent may be transmucosally delivered by the patient prior to the transitioning of at least a portion of the second solid media to a non-solid.

The layer-specific pharmaceutical agent may be, for example but without limitation, a sedative, an anesthetic, an antiemetic, a vasoconstrictor, a vasodilator, a cannabis extract, or a taste modifier. The ingestible pharmaceutical layer may also be operative to reduce a local internal body temperature following ingestion, anti-nausea medication, or other type of medicament.

According to one version of such an alternate embodiment, at least one of the portion of the first active agent made available for transmucosal delivery into the bloodstream and the portion of the second active agent may be made available for transmucosal delivery into the bloodstream is suitable for sublingual delivery into the bloodstream. According to other versions, at least one of the portion of the first active agent made available for transmucosal delivery into the bloodstream and the portion of the second active agent made available for transmucosal delivery into the bloodstream may be suitable for buccal, rectal, or urogenital delivery into the bloodstream.

According to various contemplated versions of such alternative embodiments, the second solid media may surround the entire periphery of the first solid media, or the first solid media and at least a portion of the second solid media may be enclosed within an external container. In such embodiments where the first solid media first solid media and at least a portion of the second solid media may be enclosed within an external container, the first solid media and at least the portion of the second solid media may be configured to traverse through the external container, which may comprise a tubular element.

According to further embodiments, a third solid media containing a third active agent may also be provided, the third solid media being transitionable from a solid to a non-solid at a temperature lower than the internal body temperature of the patient such that following ingestion and subsequent transition of at least a portion of the third solid media to a third non-solid media, the portion of the second active agent contained within the second non-solid media is suitable for transmucosal delivery into the bloodstream, wherein the third solid media at least partially encloses the second solid media such that following ingestion of the delivery system, no portion of the second active agent may be transmucosally delivered by the patient prior to the transitioning of at least a portion of the third solid media to a non-solid.

According to further embodiments, it is contemplated that the transition of at least one of the portion of the first solid media to a first non-solid media and the portion of the second solid media to a second non-solid media may comprise melting from a solid to a liquid phase. Alternatively, it is contemplated that the transition of at least one of the portion of the first solid media to a first non-solid media and the portion of the second solid media to a second non-solid media may comprise sublimation from a solid to a gas phase.

It is further contemplated that at least one of the first solid media and the second solid media comprises a frozen colloidal suspension, a frozen crystalloid solution, ice, acetonitrile, dimethylsulfoxide, ethanol, carbon dioxide, or glycerine.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

These and other features and advantages of the various embodiments disclosed herein are better understood with respect to the following descriptions and drawings, in which.

Common reference numerals are used throughout the drawings and the detailed description to indicate the same elements.

DETAILED DESCRIPTION

The detailed description set forth below in connection with the appended drawings is intended as a description of the presently contemplated embodiments of transmucosal pharmaceutical delivery systems, and is not intended to represent the only form in which the disclosed subject matter may be developed or utilized. The description sets forth the various functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

According to various aspects of the present disclosure, a multi-layered pharmaceutical delivery system is envisioned in which the delivery of medicaments to patients is controlled via the delivery system being constructed in order to effectuate the at-least partially sequential delivery of medicaments contained within the respective layers. According to an exemplary embodiment, a frozen ice pop is contemplated to contain an outermost ingestible pharmaceutical layer enclosing an inner ingestible pharmaceutical layer, and optionally further ingestible pharmaceutical layers sequentially enclosed within that inner pharmaceutical layer. Each layer is characterized by one or more layer-specific delivery parameters associated with a layer-specific pharmaceutical agent contained within the media of that layer. Following oral ingestion by a patient, the frozen solid media of the outer layer melts into a liquid containing the medicament, rendering that medicament available for sublingual delivery. The melting of the outer layer eventually exposes the inner layer, which subsequently may melt into a liquid, rendering the medicament within the inner layer available for sublingual delivery. Layers may also contain no active medicament, functioning instead as time-delay mechanisms, or serving to isolate layers from one another where direct contact between those layers is not preferred, for example, in circumstances where undesired reactions may occur between constituents of adjacent layers during storage or use. By adjusting the parameters of the composition and construction of the media of the layers, the time for each layer to melt and have the medicaments contained within made available to the patient, and for subsequent layers to be exposed, may be adjusted as well. In this way, it may be seen that by arraying a controlled sequence of inner layers, a controlled complex medicament delivery regime may be greatly simplified. Further, it is contemplated that the low temperature of such a contemplated embodiment may further aide in locally lowering the patient's body temperature, which may in itself also provide certain medically desirable benefits. Other embodiments are also contemplated which may enhance certain of these discussed benefits or provide other benefits.

It is also contemplated that according to other embodiments and aspects of the present disclosure, the multi-layered pharmaceutical delivery system as contemplated is not necessarily a frozen substance, but may be solid or semi-solid at room temperature and configured to dissolve, dissociate, or otherwise melt so as to have its contents made available for sublingual delivery for example, such as in a gelatinous substance such as agar, gelatin, or konnyaku, and formed to appear as gum drops, gum animals, etc. or as in a crystallized material such as a hard candy, lozenge, lollipop, etc., or encapsulated in micro encapsulation particles.

Figures 1, 2, 3, 4:
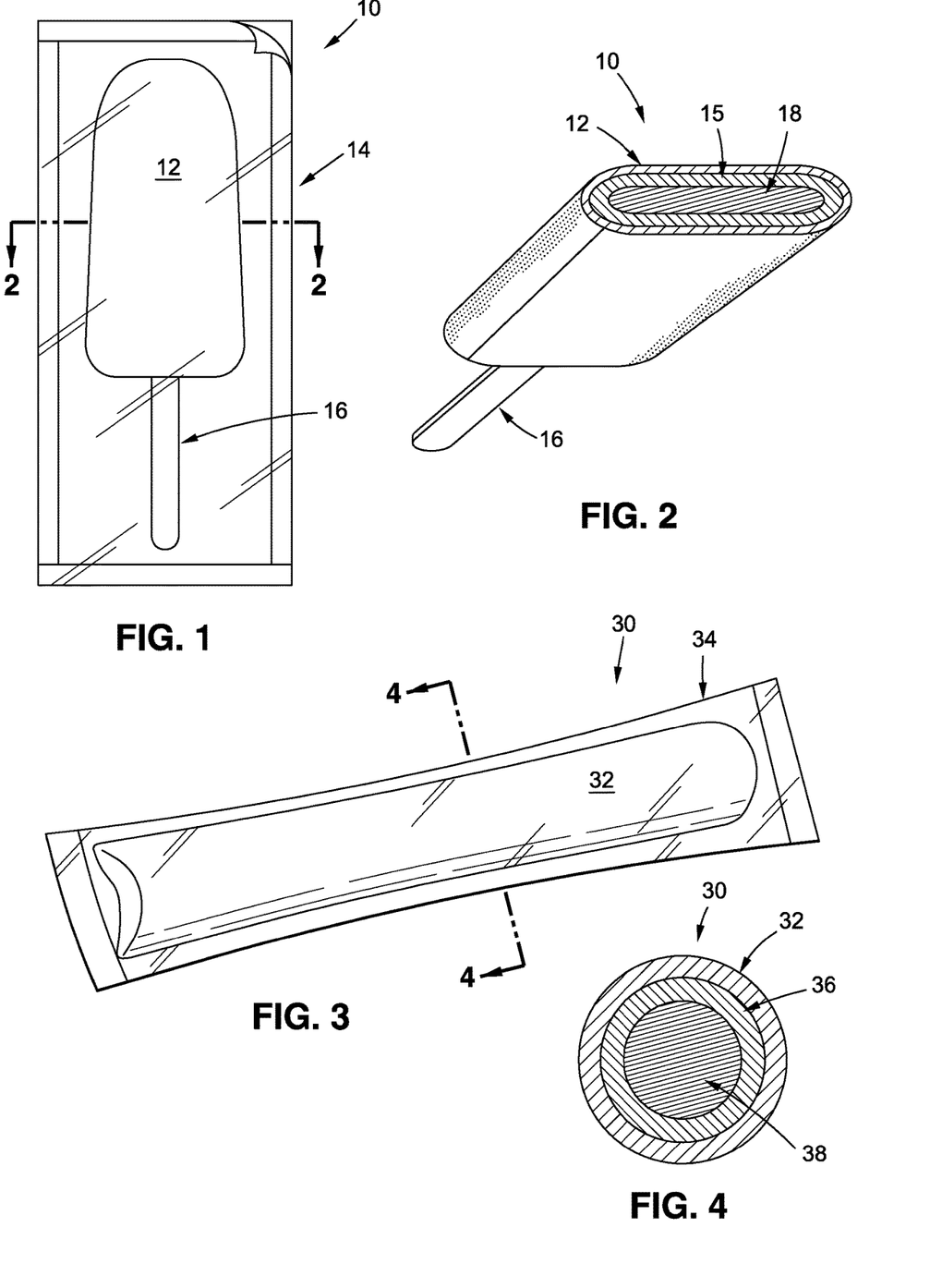
FIG. 1 is a front view of a packaged ice pop according to a first exemplary embodiment of the pharmaceutical delivery system of the present disclosure.
FIG. 2 is a perspective cross-sectional view of the first exemplary shown in FIG. 1, showing the ingestible pharmaceutical layers.
FIG. 3 is a perspective view of a packaged ice pop according to a second exemplary embodiment of the pharmaceutical delivery system of the present disclosure.
FIG. 4 is a cross-sectional view of the second exemplary embodiment shown in FIG. 3, showing the ingestible pharmaceutical layers.

Turning now to FIG. 1, a pharmaceutical delivery system 10 according to a first exemplary embodiment is shown. In this first exemplary embodiment, a pharmaceutical delivery device 10 may be structured similarly to one type of conventional frozen ice pop, wherein a plurality of pharmaceutical layers including an outermost first ingestible pharmaceutical layer 12, are enclosed within an external container 14 and frozenly affixed to a holder 16.

It may be seen that there may be substantial advantages which may flow from the use of low-temperature frozen solid media (such as ice) in forming the pharmaceutical layers, with the medicaments contained within the pharmaceutical layers and being released when the layers melt following ingestion by the patient. One of these advantages may be that the low temperature of the pharmaceutical layers may act in a numbing fashion to substantially reduce local pain. The low temperature may also act to cause local vasodilation, which may reduce inflammation. These advantages may serve to make serve to substantially increase the tolerance of a patient for such a pharmaceutical delivery system 10 compared to other modes or routes of administration, especially in cases where the patient suffers from oral mucositis, which is one of the most common side effects of chemotherapy and radiation therapy, or other oral conditions.

Turning now to FIG. 2, a cross-sectional view is shown which further illustrates how the first exemplary embodiment of a pharmaceutical delivery system 10 is constructed. Specifically, it may be seen that inside the first exemplary embodiment, a second ingestible pharmaceutical layer 15 may be enclosed within the first ingestible pharmaceutical layer 12, and a third ingestible pharmaceutical layer 18 may be enclosed within the second ingestible pharmaceutical layer 15. Once removed from the external container, the pharmaceutical delivery system 10 may be held by a patient via the holder 16 for ease of use.

Each of the ingestible pharmaceutical layers may be comprised of a media containing at least one layer-specific pharmaceutical agent. In the exemplary embodiment, there are four layers consisting sequentially, from the external layer, of an anxiolytic agent such as lorazepam, followed by a layer containing an anti-emetic agent such as ondansetron, followed by a layer containing ginger in aqueous solution, followed by a layer containing an agent given to reduce risk of allergic reaction such as diphenhydramine and/or an agent given in order to reduce pyrexia such as acetaminophen. The active compounds can be dissolved in ingestible aqueous solutions including water, organic solvent based formulations, such as containing a mixture of polyethylene glycol and glycerol 85%, or cyclodextrin, with a flavor and color additives. It may thus be seen how such devices may be tailored to provide a variety of combination for specific clinical indications.

However, it may be seen that in other embodiments, other media formulations or types of media, as well as other pharmaceutical agents may be utilized, as well as varying combinations and arrangements thereof. For example, it may be seen that medicinal cannabis, antimicrobial agents, amnestic agents for patients receiving procedures, and/or analgesic agents for post-operative or post-procedure patients may be used individually, in various combinations, and/or varying arrangements, as components of the layers of the herein contemplated pharmaceutical delivery systems. Also, pharmaceutical agents can be delivered with, or as part of the media in micro-encapsulation form. For example, powdered alcohol may be provided using micro-encapsulation as described in U.S. 3,786,159 to Sato, titled "PROCESS OF MANUFACTURING ALCOHOL CONTAINING SOLID MATTER" filed Dec. 13, 1971, the entire substance of which is incorporated herein by reference. Such an approach is considered advantageous for pharmaceuticals that are less soluble in water, but more soluble in alcohol (e.g., ethanol, etc.).

Use of frozen formulations may be especially preferred, especially for applications where it is desired to specifically reduce blood flow through the mouth area. For example, it may be seen that during treatment of patients for conditions such as stomatitis and pharyngitis, it may be desirable to cool and reduce blood flow in the mouth area in order to reduce oral complications.

The manufacturing process for the embodiment of FIGS. 1 and 2 may be achieved via a process in which the constituent layers are sequentially frozen in containers having desired sizes and configurations. For example, an innermost layer may be initially frozen with a holder placed therein in a mold or other container having an internal dimension configured to result in a desired shape and size to result in production of that innermost layer. The frozen innermost layer may be removed from the initial mold or other container and moved to a second, larger mold or other container containing the material of the second layer. By repeating this process, a final product may be realized. Alternatively, multiple layers or layer constituents may be frozen separately, and may be abutted to one another, such as by partially melting the two surfaces by exposing one or both surfaces to radiation, a warm object, or higher temperature air, and subsequently affixing them together, and refreezing the assembly. Techniques such as slowly or rapidly dropping the temperature of the layers to be frozen may be used as appropriate based on the ingredients to be frozen. However, it may be seen that in other embodiment, other processes of manufacture may be utilized, and the herein disclosed concepts are not to be limited in any fashion by the specific process of manufacture used.

Turning now to FIG. 3, a second exemplary embodiment of a pharmaceutical delivery system 30 is shown. In this second exemplary embodiment, a different form of frozen ice pop is utilized, in which it may be seen that instead of being frozenly affixed to a holder, the pharmaceutical delivery system 30 may be held via the external container 34, with the pharmaceutical layers, including at least a first pharmaceutical layer 32, being advanced through the external container 34 during use as they are ingested by the patient. Alternatively, the external container 34 may be disposed of, and the pharmaceutical delivery system 30 may be deposited in a fluid such as water or another consumable beverage. In this alternate method of consumption, it may be seen how the progressive layers may melt, dissolve, or otherwise transition into the surrounding fluid. By the progressive consumption of the surrounding fluid, the patient will receive the components of the progressive layers in a time-delayed manner, with the surrounding fluid initially containing only the outermost layer's components, followed by a combination of the outermost layer with the components of the successive inner layers.

Turning now to FIG. 4, a cross-sectional view of the second exemplary embodiment illustrated by FIG. 3 is shown. It may be seen that, similarly to the first exemplary embodiment illustrated in FIGS. 1 and 2, multiple pharmaceutical layers may be enclosed within one another in the pharmaceutical delivery system 30, such as a first pharmaceutical layer 32, a second pharmaceutical layer 36, and a third pharmaceutical layer 38, which may achieve a time-delay in administration of the pharmaceutical agent contained within the respective media of each layer, depending on the layer-specific delivery parameters of each layer. For example, by configuring the layers to be thinner or thicker, it may be seen that administration of that layer and/or subsequently layers may be prolonged or delayed, or shortened or more rapid. Likewise, the choice of media itself may also quicken or prolong the time to administer that layer, for example, by using a media which transitions from a solid to a fluid more or less rapidly. For example, if a water-based media is used, components may be added to the water-based media as part of or in addition to the pharmaceutical agent which results in freezing point elevation or depression, which would affect the transition time of the water-based media from ice to water when ingested by the patient. In the alternative, a media that is not entirely water-based may be used, or not water-based at all, which would have a different melting or sublimation point when ingested by the patient. For example, the addition of ethanol to water may lower the freezing point of the media compared to water alone, or the use of frozen dimethyl sulfoxide (DMSO) as the media may result in a media having a higher freezing point than water alone.

Figure 5:
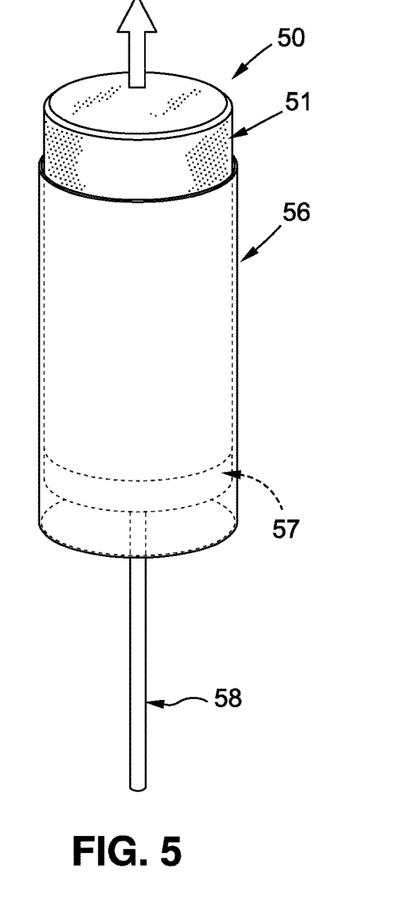
FIG. 5 is a perspective view of a packaged frozen ice pop according to a third exemplary embodiment of the pharmaceutical delivery system of the present disclosure.

Turning now to FIG. 5, a third exemplary embodiment of a pharmaceutical delivery system 50 is disclosed, in which the pharmaceutical layers are arranged in linear sequence, rather than being fully enclosed within one another. It may be seen that, for example, such an arrangement may be utilized in embodiments resembling conventional "pusher" frozen ice pop confections. For example, it may be seen that such embodiments may have the pharmaceutical layers, including at least a first pharmaceutical layer 51, arranged enclosed within an external container 56 in a cylinder or other shape, with a pusher 57 attached to a holder 58, whereby the user may advance the pharmaceutical layers sequentially through the external container 56 so that they may become sequentially accessible to the patient following the ingestion of the prior layer.

Figure 6:
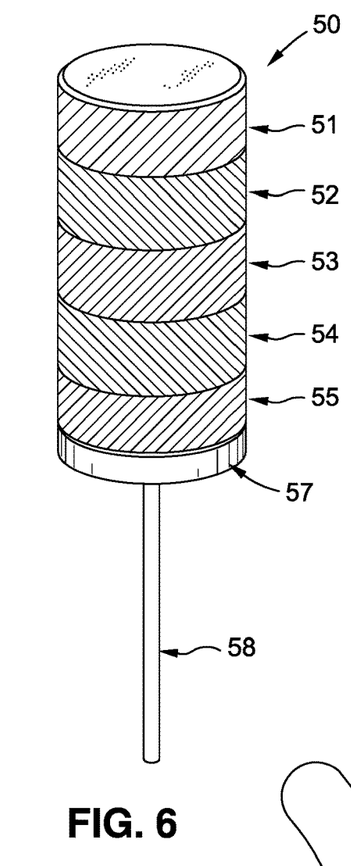
FIG. 6 is a perspective cut-away view of the third exemplary embodiment shown in FIG. 5, showing the ingestible pharmaceutical layers.

Turning now to FIG. 6, which illustrates the portion of the third exemplary embodiment shown in FIG. 5 enclosed within the external container, it may be seen how in the pharmaceutical delivery system 50 the pharmaceutical layers may be arranged linearly in sequence in a fashion that may permit more prolonged administration of each individual layer, or the administration of a greater amount of physical layers, due to the physical structure of the embodiment. It may be seen how as the pharmaceutical layers are advanced through the external container via the pusher 57 actuated by applying pressure to the holder 58, those pharmaceutical layers may be sequentially exposed in a desired order of delivery. In the illustrated embodiment, a first pharmaceutical layer 51 is initially delivered, followed in sequence by a second pharmaceutical layer 52, a third pharmaceutical layer 53, a fourth pharmaceutical layer 54, and a fifth pharmaceutical layer 55.

Figure 7:
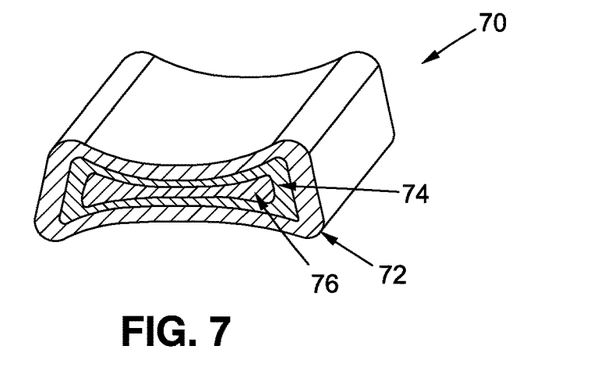
FIG. 7 is a perspective cut-away view of a fourth exemplary embodiment the pharmaceutical delivery system of the present disclosure.

Turning now to FIG. 7, it may be seen that in a fourth exemplary embodiment, the pharmaceutical delivery system 70 may be delivered in a form preferably suitable for sublingual placement. As may be seen by this fourth exemplary embodiment, it may be seen that the pharmaceutical delivery system 70 may be configured to have an overall shape configured based upon the dimension of the specific patient's body, such as via a mold taken of the patient's sublingual space, mouth, or via other methods of determining the physical structural of a patient's sublingual or transmucosal-adjacent spaces, such as various imaging technologies. It is further contemplated that in connection with such imaging technologies, techniques such as 3D printing may be utilized to generate a pharmaceutical delivery system 70, personalized according to the results of the imaging technology. In this fourth exemplary embodiment, it may be seen how due to the internal construction of the pharmaceutical delivery system, the pharmaceutical layers may deliver medication according to a predefined sequence. Following sublingual placement, the outermost first pharmaceutical layer 72 may initially deliver medication to the patient, followed by the second pharmaceutical layer 74, followed by the third pharmaceutical layer 76.

Figure 8:
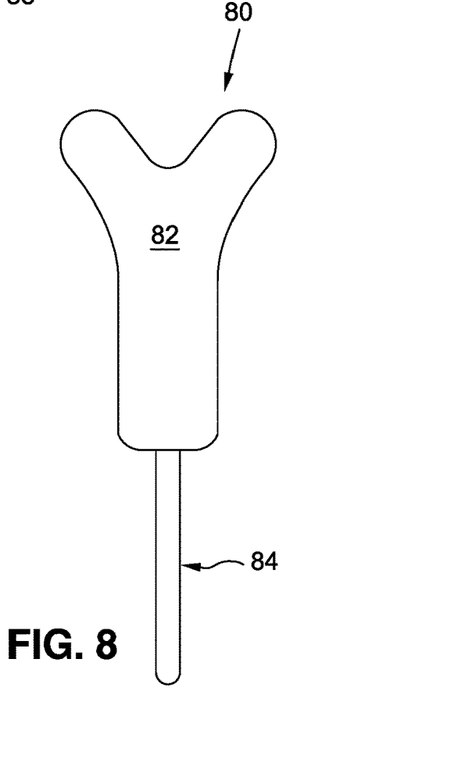
FIG. 8 is a front view of an ice pop according to a fifth exemplary of the pharmaceutical delivery system of the present disclosure.

Turning now to FIG. 8, a fifth exemplary embodiment of a pharmaceutical delivery system 80 configured for sublingual placement is shown. As may be seen, the forked shape of the pharmaceutical delivery system 80 of this fifth exemplary embodiment may also permit sublingual placement and may maximize contact of the first pharmaceutical layer 82 with a patient's sublingual region, but may also permit the periodic removal of the pharmaceutical delivery system 80 by the patient using a holder 84.

Figure 9:
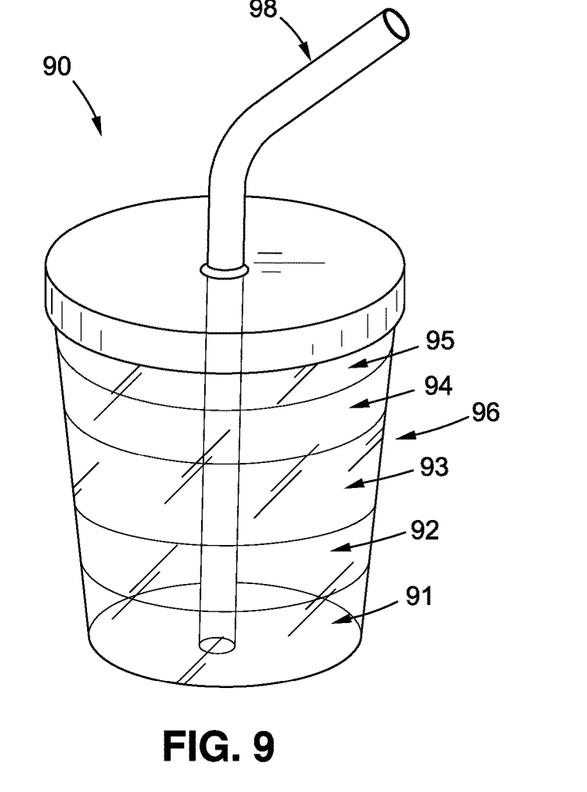
FIG. 9 is a perspective line-drawing view of a sixth exemplary embodiment of the pharmaceutical delivery system of the present disclosure.

Turning now to FIG. 9, a sixth exemplary embodiment of a pharmaceutical delivery system 90 is shown, wherein the ingestible pharmaceutical layers are arranged inside an external container 96 in a sequential fashion configured to permit the pharmaceutical layers, once sufficiently liquid, to be ingested by the patient via a straw 98. It may be seen that in this sixth exemplary embodiment, by controlling and/or fixing the depth of the straw 98, the patient may sequentially ingest the pharmaceutical layers from the bottom upward, with the first pharmaceutical layer 91 being initially delivered to the patient, followed by the second pharmaceutical layer 92, the third pharmaceutical layer 93, the fourth pharmaceutical layer 94, and the fifth pharmaceutical layer 95. The straw 98 may be vertically fixed in certain embodiments, in order to aid in properly sequencing the order of delivery of the medicaments in the pharmaceutical layers.

Figure 10:
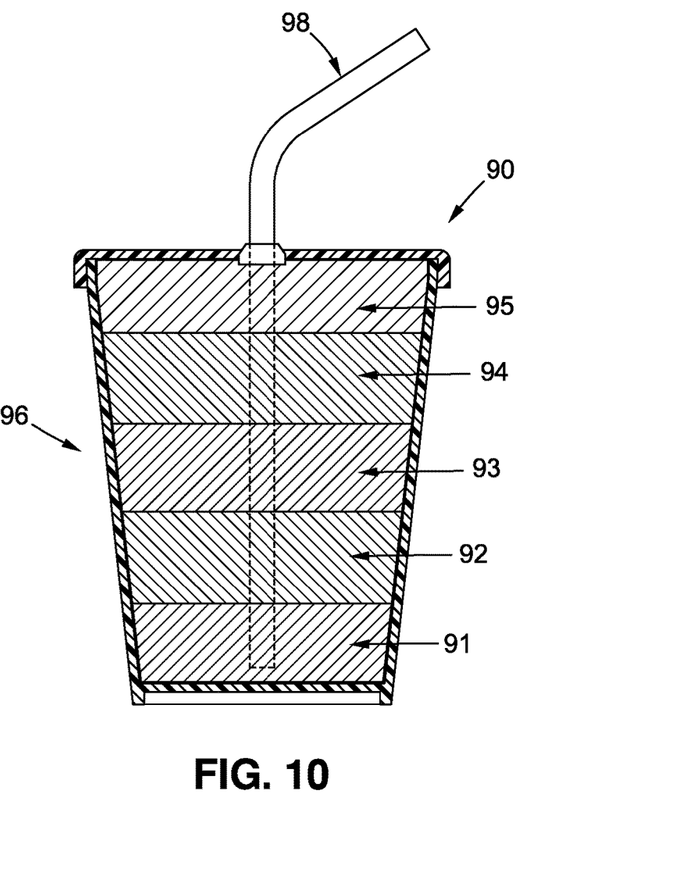
FIG. 10 is a front cross-sectional view of the sixth exemplary embodiment shown in FIG. 9, showing the ingestible pharmaceutical layers.

Turning now to FIG. 10, a cross-sectional view of the sixth exemplary embodiment shown in FIG. 9 is depicted. As may be seen, in the sixth exemplary embodiment, by fixing the depth of the straw 98 at a level sufficient to permit intake of the components of the sequential pharmaceutical layers 91, 92, 93, 94, 95 once they are sufficiently liquefied, granulated, or otherwise reduced in viscosity so as to permit intake in the space between the bottom of the straw 108 and the external container 96, the sequential order delivery may be enforced. The disclosure contemplates that the layers of medicament may be attached to the inner sides of a cup for dissipation or interaction into the cup contents. In addition, straw 98 may include layers of medicament to interact or dissolve into the cup contents.

Figure 11:
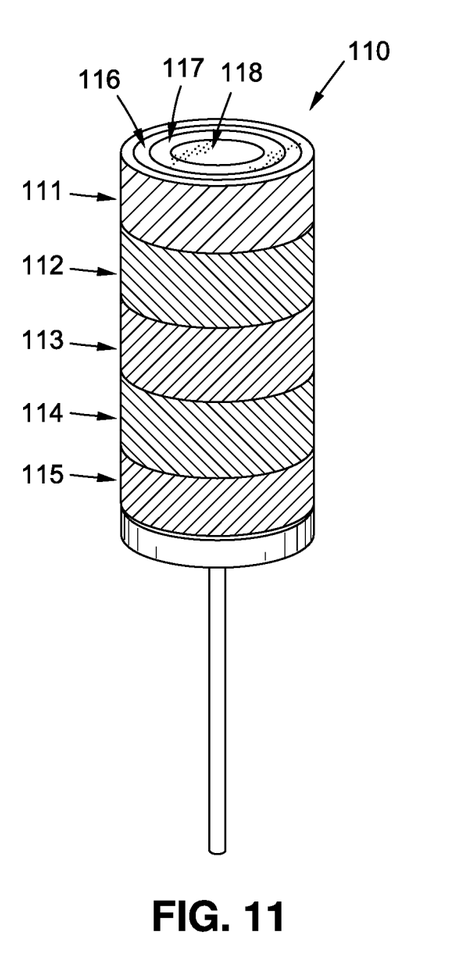
FIG. 11 is a perspective line-drawing view of a seventh exemplary embodiment of the pharmaceutical delivery system of the present disclosure.

Turning now to FIG. 11, a seventh exemplary embodiment of a pharmaceutical delivery system 110 is illustrated. This seventh exemplary embodiment, which is externally similar to the above described third exemplary embodiment shown in FIGS. 5 and 6, and is utilized in a similar fashion by a patient, shows how the various concepts of the above described embodiments may be combined together or modified to achieve specific desired purposes, all of such combinations falling within the scope and spirit of this disclosure. It may be seen how in this seventh exemplary embodiment, the order of delivery of the components of the pharmaceutical layers may be modified not just by sequentially delivering vertically oriented layers as in FIGS. 5 and 6, but those layers themselves may also be configured to contain sub-layers so as to permit various medicaments or other components to be delivered in sub-sequences. As may be seen, as the pharmaceutical delivery system 110 is advanced through an external container and consumed, the first pharmaceutical layer 111 is initially exposed, followed by the second pharmaceutical layer 112, the third pharmaceutical layer 113, the fourth pharmaceutical layer 114, and the fifth pharmaceutical layer 115. During the consumption of each of those pharmaceutical layers, however, internal layers are also consumed in sequence. For example, following the consumption of the first pharmaceutical layer 111, but before consumption of second pharmaceutical layer 112, a sequence of pharmaceutical sublayers 116, 117, and 118 may be consumed. This interposing and sub-sequencing may reoccur during the consumption of each pharmaceutical layer.

Figure 12:
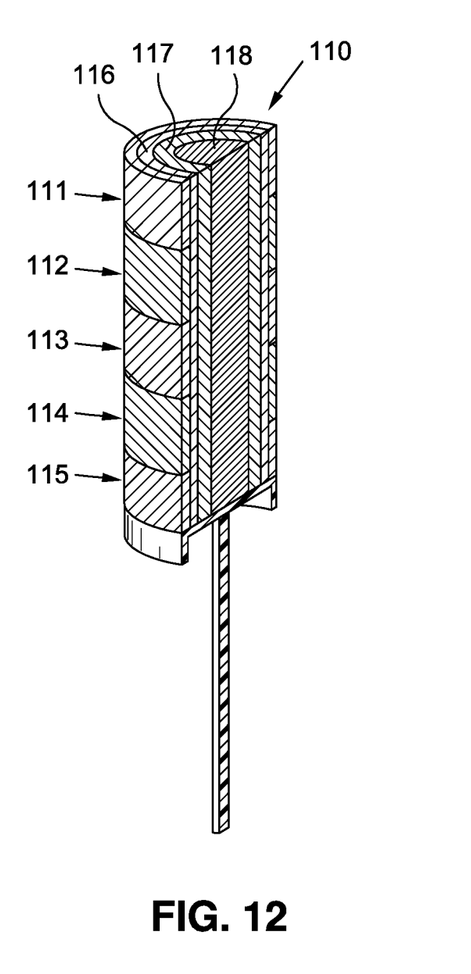
FIG. 12 is a perspective cross-sectional view of the seventh exemplary embodiment shown in FIG. 11, showing the ingestible pharmaceutical layers and sublayers.

Turning now to FIG. 12, a cut-away view of the seventh exemplary embodiment illustrated in FIG. 11 is shown, illustrating one possible way in which the pharmaceutical sublayers of the pharmaceutical delivery system 110 may be arranged. It may be seen that in the illustrated embodiment, each of the pharmaceutical sublayers 116, 117, 118 is continuous throughout the vertical length of the pharmaceutical delivery system 110. Thus, it may be seen that immediately following consumption of the pharmaceutical layers 111, 112, 113, 114, and 115, a patient will sequentially consume the pharmaceutical sublayers 116, 117, and 118 prior to returning to consumption of the next pharmaceutical layer. In the illustrated embodiment, it may be seen that the vertical continuity of the three illustrated pharmaceutical sublayers 116, 117, 118 throughout the pharmaceutical delivery system 110 may result in a repeated sequential consumption of the included components within those three pharmaceutical sublayers 116, 117, and 118 between consumption of the pharmaceutical layers. However, it may be seen that in other embodiment, some of or all of the pharmaceutical sublayers may not be vertically continuous, or may be omitted entirely. For example, it is readily conceivable that certain pharmaceutical layers may be continuous across the horizontal radius of the pharmaceutical delivery system 110 for specific purpose, such as in order to administer a greater amount of medicament or to extend the time in which that layer is consumed. It is also readily conceivable that in an embodiment in which the pharmaceutical sublayers are not vertically continuous, each pharmaceutical layer 111, 112, 113, 114, 125 may have its own unique combination of pharmaceutical sublayers, which may permit sequential delivery patterns of even greater complexity. Thus, by varying the construction of the pharmaceutical delivery system, other parameters of delivery may be varied in accordance therewith.

It should also be appreciated that other embodiments are readily conceivable, including embodiments that contain multiple different pharmaceutical layers that are or may be exposed to the patient simultaneously, which may permit not only sequential drug delivery, but simultaneously timed drug delivery. It is additionally contemplated that other inclusions may be present on or within one or more of the various layers of the pharmaceutically delivery systems, including inclusions that are positioned atop or across layers, or distributed throughout some or all of the layers. Such inclusions may take the physical of, for example but without limitations, stripes, rings, and dots on or within the various layers of the pharmaceutical delivery system. It may be readily seen how the presence of such inclusions may affect the final drug delivery profile of the pharmaceutical delivery system and lead to the delivery of different combinations of drugs at varying time periods.

Figure 13:
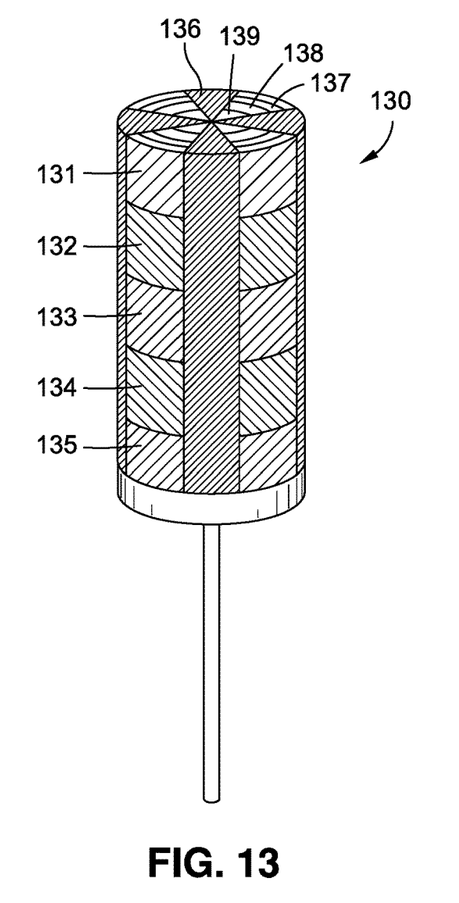
FIG. 13 is a perspective line-drawing view of an eighth exemplary embodiment of the pharmaceutical delivery system of the present disclosure.

For example, turning now to FIG. 13, a perspective view of an eighth exemplary embodiment of a pharmaceutical delivery system 130 is illustrated, illustrating another possible way in which the pharmaceutical sublayers of the pharmaceutical delivery system 130 may be arranged. According to the eighth exemplary embodiment, it may be seen that each of the first pharmaceutical layer 111, the second pharmaceutical layer 112, the third pharmaceutical layer 113, the fourth pharmaceutical layer 114, and the fifth pharmaceutical layer 115 are divided by the presence of a vertically continuous radial region 136 that emanates from the center outwards. There additionally may be a series of pharmaceutical sublayers 137, 138, and 139 in the regions not occupied by the radial region 136. It may be seen that this eighth exemplary embodiment may permit continuous consumption of any medicaments contained within the radial region 136 throughout the period in which the pharmaceutical delivery system is ingested by the patient, while maintaining a variation in the sequence of delivery of any medicaments contained within the other pharmaceutical layers and sublayers.

Figure 14:
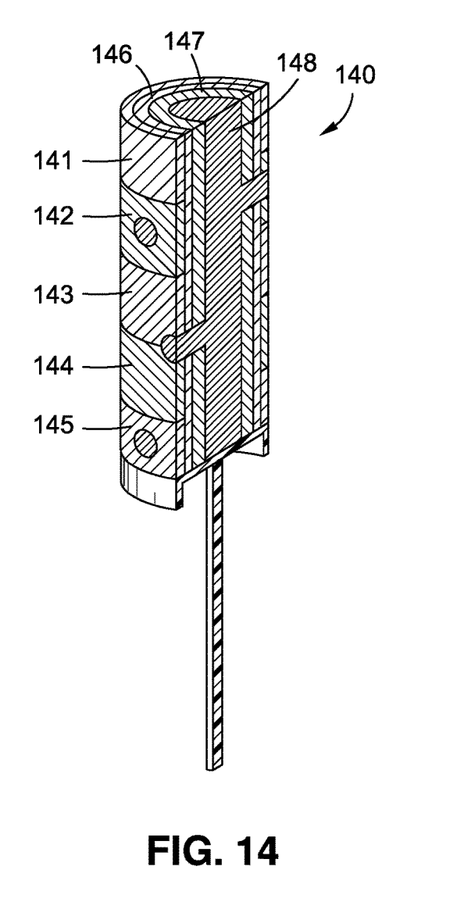
FIG. 14 is a perspective cross-sectional view of a ninth exemplary embodiment of the pharmaceutical delivery system of the present disclosure.

Turning now to FIG. 14, a perspective cut-away view of a ninth exemplary embodiment of a pharmaceutical delivery system 140 is illustrated. It may be seen that the ninth exemplary embodiment bears a similar configuration to the seventh exemplary embodiment, with a sequence of pharmaceutical layers 141, 142, 143, 144, 145 arranged vertically, and with a series of vertically continuous pharmaceutically sublayers 146, 147, 148 arranged radially inward. However it may be seen that in this ninth exemplary embodiment, the innermost pharmaceutical sublayer 148 may at portions protrudes outward to the perimeter of the pharmaceutical delivery system. In this way, it may be seen that a similar sequence of medication delivery to the seventh exemplary embodiment may be realized, except with a constant, staggered delivery of the medicament contained in pharmaceutical sublayer 148, with some delivery at all times due to consumption of the protruding portions, and with elevated periods of delivery when the inner core region of the pharmaceutical sublayer 148 are accessed and consumed by the patient.

Figure 15:
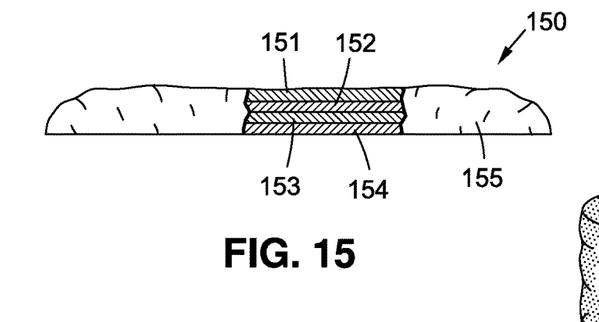
FIG. 15 is a front cross-sectional view of a tenth exemplary embodiment of the pharmaceutical delivery system of the present disclosure.

Turning now to FIG. 15, a front partial cut-away view of a tenth exemplary embodiment of a pharmaceutical delivery system 150 is illustrated. As may be seen, it is contemplated that according to certain aspects of the present disclosure, a pharmaceutical delivery system 150 may comprise further different arrangements of the pharmaceutical layers 151, 152, 153, 154. For example, it may be seen that the layers may be vertically arranged in a disk-like configuration, optionally with a surrounding pharmaceutical layer 155 which may or may not contain further medicaments. It may be seen that such embodiments may, for example, permit a sequence of delivery whereby there is a first simultaneous delivery of the medicaments contained within the two outer pharmaceutical layers 151, 154, followed by the simultaneous delivery of the medicaments contained within the two inner pharmaceutical layers 152, 153.

Figure 16:
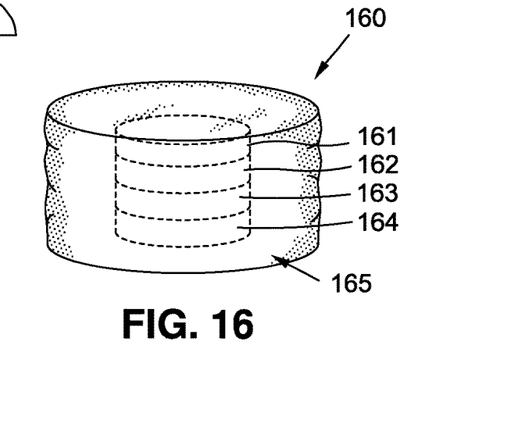
FIG. 16 is a perspective x-ray view of an eleventh exemplary embodiment of the pharmaceutical delivery system of the present disclosure.

Turning now to FIG. 16, a perspective x-ray view of an eleventh exemplary embodiment of a pharmaceutical delivery system 160 is shown. Similarly to the tenth exemplary embodiment, the eleventh exemplary embodiment may include a series of vertically arranged disk-shaped pharmaceutical layers 161, 162, 163, 164. However, it may be seen that the overall shape of the eleventh exemplary embodiment may differ in that it may be substantially thicker, rather than a thinner platen shape, with a more substantial surrounding pharmaceutical layer 160. It may thus be seen that the eleventh exemplary embodiment may permit, for example, a sequence of delivery where, once the surrounding pharmaceutical layer 165 has been substantially dissolved or melted, the simultaneous delivery of the medicaments contained within the outer pharmaceutical layers 161, 164 with some moderate, lesser delivery of the medicaments contained within the inner pharmaceutical layers 162, 163, followed, by a simultaneous increase in rate of delivery of the medicaments contained within the inner pharmaceutical layers once the outer pharmaceutical layers 161, 164 have been consumed.

It is further contemplated that in accordance with the embodiments of the present disclosure, any of the above described embodiments, alone or in combination with one another, may be individually tailored to the specific patient depending the individual patient's needs, and as such a pharmaceutical delivery system may even be created "on-demand" in accordance with and customized to a patient's medical needs. In connection therewith, it is contemplated that patients and/or a patient's medical provider (such as a doctor a pharmacy) may be provided with instructions for creating a particularized version of a pharmaceutical delivery system rather than the patient being directly provided with the delivery system at the time of use. For example, a patient may be provided with a customized mold which may serve as a container and also adapted for creating a pharmaceutical delivery system which may be used along with a standardized manufacturing system, along with instructions for how to use the standardized manufacturing system with the customized mold to create a custom pharmaceutical delivery system tailored for that patient's specific medical needs via containing specific arrangements and quantities of medicaments. It is additionally contemplated that the patient and/or the mold provided to the patient may be provided with particular markings such as a patient identifier, medicament identifier, etc. which may contain such instructions, and that in more particular embodiments, such markings may be, for example but without limitation, a bar code or a QR code readable by a standardized manufacturing system for the automated creation of a pharmaceutical delivery system customized for that particular patient in accordance with the prescription directed to that patient. Such marking may also be placed on the pharmaceutical delivery system itself, to aid in tracking of customized versions and to prevent inadvertent mistakes. The container/mold could be constructed to protect temperature sensitive parts such as teeth.

In some embodiments, the numbers expressing dimensions, quantities, quantiles of ingredients, properties of materials, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclose may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the disclosure and does not pose a limitation on the scope of the claimed inventive subject matter. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The discussion herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Various objects, features, aspects and advantages of the inventive subject matter will become more apparent from the following detailed description of preferred embodiments, along with the accompanying drawing figures in which like numerals represent like components.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The above description is given by way of example, and not limitation. Given the above disclosure, one skilled in the art could devise variations that are within the scope and spirit of the inventive subject matter disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A pharmaceutical delivery system comprising:
an outermost ingestible pharmaceutical layer comprising a media containing an anxiolytic agent;
an intermediate ingestible pharmaceutical layer comprising a media containing an anti-emetic agent; and
an innermost ingestible pharmaceutical layer comprising a media containing an agent to reduce risk of allergic reaction;
wherein the media of at least one of the outermost ingestible pharmaceutical layer, the second ingestible pharmaceutical layer, or the innermost ingestible pharmaceutical layer comprises a frozen colloidal suspension;
wherein the media of at least one of the outermost ingestible pharmaceutical layer, the second ingestible pharmaceutical layer, or the innermost ingestible pharmaceutical layer comprises a frozen crystalloid solution;
wherein the media of at least one of the outermost ingestible pharmaceutical layer, the second ingestible pharmaceutical layer, or the innermost ingestible pharmaceutical layer comprises ethanol and has a melting point at or below $-10°$ C.; and
wherein the media of at least one of the outermost ingestible pharmaceutical layer, the second ingestible pharmaceutical layer, or the innermost ingestible pharmaceutical layer comprises dimethyl sulfoxide and has a melting point above $-10°$ C.

2. The pharmaceutical delivery system of claim 1, wherein the media of at least one of the outermost ingestible pharmaceutical layer, the intermediate ingestible pharmaceutical layer, or the innermost ingestible pharmaceutical layer comprises ice.

3. The pharmaceutical delivery system of claim 1 further comprising an additional intermediate ingestible layer comprising ginger in aqueous solution.

4. The pharmaceutical delivery system of claim 1, wherein the media of at least one of the outermost ingestible pharmaceutical layer, the intermediate ingestible pharmaceutical layer, or the innermost ingestible pharmaceutical layer comprises glycerine.

5. The pharmaceutical delivery system of claim 1, wherein the media of at least one of the outermost ingestible pharmaceutical layer, the intermediate ingestible pharmaceutical layer, or the innermost ingestible pharmaceutical layer comprises a lipid.

6. The pharmaceutical delivery system of claim 1, wherein at least one of the outermost ingestible pharmaceutical layer, the intermediate ingestible pharmaceutical layer, or the innermost ingestible pharmaceutical layer is characterized by one or more layer specific delivery parameters associated with the media of that layer and/or the agent contained within that layer, and wherein at least one of the one or more layer-specific delivery parameters comprises availability for transmucosal delivery into the bloodstream.

7. The pharmaceutical delivery system of claim 6, wherein the transmucosal delivery comprises sublingual delivery.

8. The pharmaceutical delivery system of claim 6, wherein the transmucosal delivery comprises buccal delivery.

9. The pharmaceutical delivery system of claim 6, wherein the transmucosal delivery comprises rectal delivery.

10. The pharmaceutical delivery system of claim 6, wherein the transmucosal delivery comprises urogenital delivery.

11. The pharmaceutical delivery system of claim 6, wherein one of the one or more layer-specific delivery parameters comprises a time to melt at a specified temperature.

12. The pharmaceutical delivery system of claim 6, wherein one of the one or more layer-specific delivery parameters comprises a time to dissolve.

13. The pharmaceutical delivery system of claim 6, wherein one of the one or more layer-specific delivery parameters comprises a thickness.

14. A method of administering a pharmaceutical delivery system to a patient, comprising the step of
   administering to the patient the pharmaceutical delivery system of claim 1.

* * * * *